United States Patent
Chreene et al.

(10) Patent No.: US 8,821,491 B2
(45) Date of Patent: Sep. 2, 2014

(54) DOUBLE ACTION EXTERNAL FIXATION CLAMP

(75) Inventors: David Edward Chreene, Hernando, MS (US); Gene Edward Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/813,213

(22) PCT Filed: Jul. 28, 2011

(86) PCT No.: PCT/US2011/045723
§ 371 (c)(1),
(2), (4) Date: May 13, 2013

(87) PCT Pub. No.: WO2012/016041
PCT Pub. Date: Feb. 2, 2012

(65) Prior Publication Data
US 2013/0226179 A1      Aug. 29, 2013

Related U.S. Application Data

(60) Provisional application No. 61/369,359, filed on Jul. 30, 2010.

(51) Int. Cl.
*A61B 17/00* (2006.01)

(52) U.S. Cl.
USPC .............................................. 606/59; 606/54

(58) Field of Classification Search
CPC .... A61B 17/62; A61B 17/64; A61B 17/6408; A61B 17/6425; A61B 17/6433; A61B 17/6441; A61B 17/645; A61B 17/6491; A61B 17/6475; A61B 17/6483; A61B 17/6466; A61B 17/6416
USPC .............. 606/54–59; 403/190, 191, 399, 395, 403/373, 256, 258, 260, 234–236
See application file for complete search history.

(56) References Cited

U.S. PATENT DOCUMENTS

| | | | |
|---|---|---|---|
| 6,080,153 A | 6/2000 | Mata et al. | |
| 6,652,523 B1 * | 11/2003 | Evrard et al. | 606/54 |
| 7,004,943 B2 | 2/2006 | Ferrante et al. | |
| 7,048,735 B2 | 5/2006 | Ferrante et al. | |
| 7,527,626 B2 * | 5/2009 | Lutz et al. | 606/54 |
| 7,618,417 B2 * | 11/2009 | Thomke et al. | 606/59 |
| 7,708,736 B2 | 5/2010 | Mullaney | |
| 7,758,582 B2 | 7/2010 | Ferrante et al. | |
| 2002/0077629 A1 * | 6/2002 | Hoffman et al. | 606/59 |
| 2005/0119656 A1 | 6/2005 | Ferrante et al. | |

(Continued)

OTHER PUBLICATIONS

Authorized officer Ryu, Chang Yong, International Search Report/Written Opinion in PCT/US2011/045723, mailed Mar. 27, 2012, 15 pages.

*Primary Examiner* — Jan Christopher Merene
(74) *Attorney, Agent, or Firm* — Fish & Richardson P.C.

(57) ABSTRACT

An external fixation component includes a capture member defining opposing grooves on opposite lateral sides of the capture member for capture of an element of an orthopedic fixation system. The capture member includes a base and a head coupled to the base to define a component axis that extends through the base and through the head. The base and the head are coupled for relative lateral translation in opposing directions such that the element can be captured by the capture member in either of the opposing grooves.

21 Claims, 7 Drawing Sheets

(56) References Cited

U.S. PATENT DOCUMENTS

| | | | |
|---|---|---|---|
| 2006/0052781 A1* | 3/2006 | Thomke et al. | 606/59 |
| 2006/0287652 A1* | 12/2006 | Lessig et al. | 606/54 |
| 2008/0247818 A1* | 10/2008 | Oesch et al. | 403/389 |
| 2009/0018541 A1* | 1/2009 | Lavi | 606/59 |
| 2011/0066151 A1 | 3/2011 | Mürner et al. | |

* cited by examiner

DOUBLE ACTION EXTERNAL FIXATION CLAMP

CROSS-REFERENCE TO RELATED APPLICATIONS

This application is a national stage entry under 35 U.S.C. §371 of PCT Application No. PCT/US2011/045723, filed Jul. 28, 2011, which claims the benefit of U.S. Provisional Patent Application Ser. No. 61/369,359, filed Jul. 30, 2010.

FIELD

This description relates to a double action external fixation clamp.

BACKGROUND

Surgeons use external fixation systems to treat certain bony skeletal injuries or conditions, such as acute fractures of the skeleton, soft tissue injuries, delayed union of the skeleton when bones are slow to heal, nonunion of the skeleton when bones have not healed, malunion of broken or fractured bones, congenital deformities resulting in malposition of bone, and bone lengthening, widening, or twisting. These systems typically include a frame formed by fixation components coupling one or more of a bar, rod, wire or pin.

Generally, one or more bone pins or wires are inserted into the tissue and bone and then the remainder of the fixation system is assembled. In many cases, two pins are inserted below the fracture and two pins are inserted above the fracture. The surgeon then attaches a fixation component to each pin, bridging the fixation components together with rods or bars. These bars form the frame of the external fixation system. Fracture patterns are infinite and may require the fixation system to move in multiple planes simultaneously in order to stabilize and reduce the fracture properly.

SUMMARY

In one general aspect, an external fixation component includes a capture member defining opposing grooves on opposite lateral sides of the capture member for capture of an element, for example, a bar, rod, wire or pin, of an orthopedic fixation system by snapping onto the element from a direction generally perpendicular to a longitudinal axis of the element. The capture member includes a base and a head coupled to the base to define a component axis that extends through the base and through the head. The base and the head are coupled for relative lateral translation therebetween in opposing directions not along the component axis such that the element can be captured by the capture member in either of the opposing grooves.

In another general aspect, an external fixation component includes a capture member defining opposing grooves on opposite lateral sides of the capture member for capture of an element of an orthopedic fixation system. The capture member includes a base and a head coupled to the base to define a component axis that extends through the base and through the head. The base and the head are coupled for relative lateral translation in opposing directions such that the element can be captured by the capture member in either of the opposing grooves.

Embodiments can optionally include one or more of the following features. The grooves are each configured to receive one of a bar, a rod, a wire, or a pin. One of the opposing grooves is sized to capture an element having a first diameter, and the opposing groove is sized to capture an element having a diameter greater than the first diameter. The opposing directions are perpendicular to the component axis. The external fixation component further includes a spring acting between the head and the base. Lateral translation of the head relative to the base in either of the opposing directions compresses the spring. The head defines a recess configured to receive a portion of the spring and to permit lateral flexion of the spring within the recess. The external fixation component further includes two springs acting between the head and the base, the springs extending substantially parallel to the directions of lateral translation. The head defines an oblong-shaped aperture to receive a bolt. The external fixation device further includes: a second capture member; a bolt extending along the component axis; and an internally-threaded receiving shaft. The bolt and the receiving shaft couple the capture members along the component axis. The second capture member includes a base, and an inner side of the base of the capture member engages an inner side of the base of the second capture member.

The inner sides include ridges configured to engage to fix the relative position of the capture members about the component axis. The head includes a metal frame and a portion of the metal frame is overmolded with a polymer coating. The head defines parallel channels and the base includes parallel rails that are received in the channels to slidably couple the head to the base. The engagement between the rails and the channels impedes the head from separating from the base along the component axis and impedes the head from rotating relative to the base.

The external fixation device further includes one or more springs located between the head and the base acting to couple the head to the base. Each groove is defined by channel of the head and a channel of the base. The base extends farther than the head in a neutral position of the capture member. The base and the head define an opening at the entrance to each of the opposing grooves. The capture member is configured to capture the element by snapping onto the element from a direction generally perpendicular to a longitudinal axis of the element. The base and the head are coupled for relative lateral translation in opposing directions not along the component axis.

In another general aspect, a method of capturing an external fixation element includes engaging the element with an external fixation device having a head and a base defining opposite grooves on opposite lateral sides of the external fixation device and being coupled for relative lateral translation in opposing directions. The element is moved relative to the external fixation device while in engagement with the external fixation device such that the head translates relative to the base in one of the opposing directions. The element is positioned in one of the grooves of the external fixation device such that the external fixation device captures the element.

Embodiments can optionally include one or more of the following features. Engaging the element with an external fixation device includes engaging the element in a direction generally perpendicular to a longitudinal axis of the element. Moving the element relative to the external fixation device while in engagement with the external fixation device includes compressing a spring acting between the head and the base. Positioning the element in a groove of the external fixation device includes positioning the element in the groove such that the spring moves the head relative to the base to capture the element. Positioning the element in one of the grooves of the external fixation device such that the external fixation device captures the element includes positioning the element such that the head translates relative to the base in the other of the opposing directions. Positioning the element in one of the grooves of the external fixation device such that the external fixation device captures the element includes positioning the element such that the external fixation device snaps onto the element.

Advantageous implementations can include one or more of the following features. An external fixation element can be quickly and securely coupled to an external fixation device. An external fixation element can be coupled to the external fixation device at a predetermined orientation. An external fixation element can be captured by an external fixation device snapping onto the element from a direction generally perpendicular to a longitudinal axis of the element.

The details of one or more embodiments are set forth in the accompanying drawings and the description below. Other features, objects, and advantages will be apparent from the description and drawings, and from the claims.

DETAILED DESCRIPTION

Figure 1:
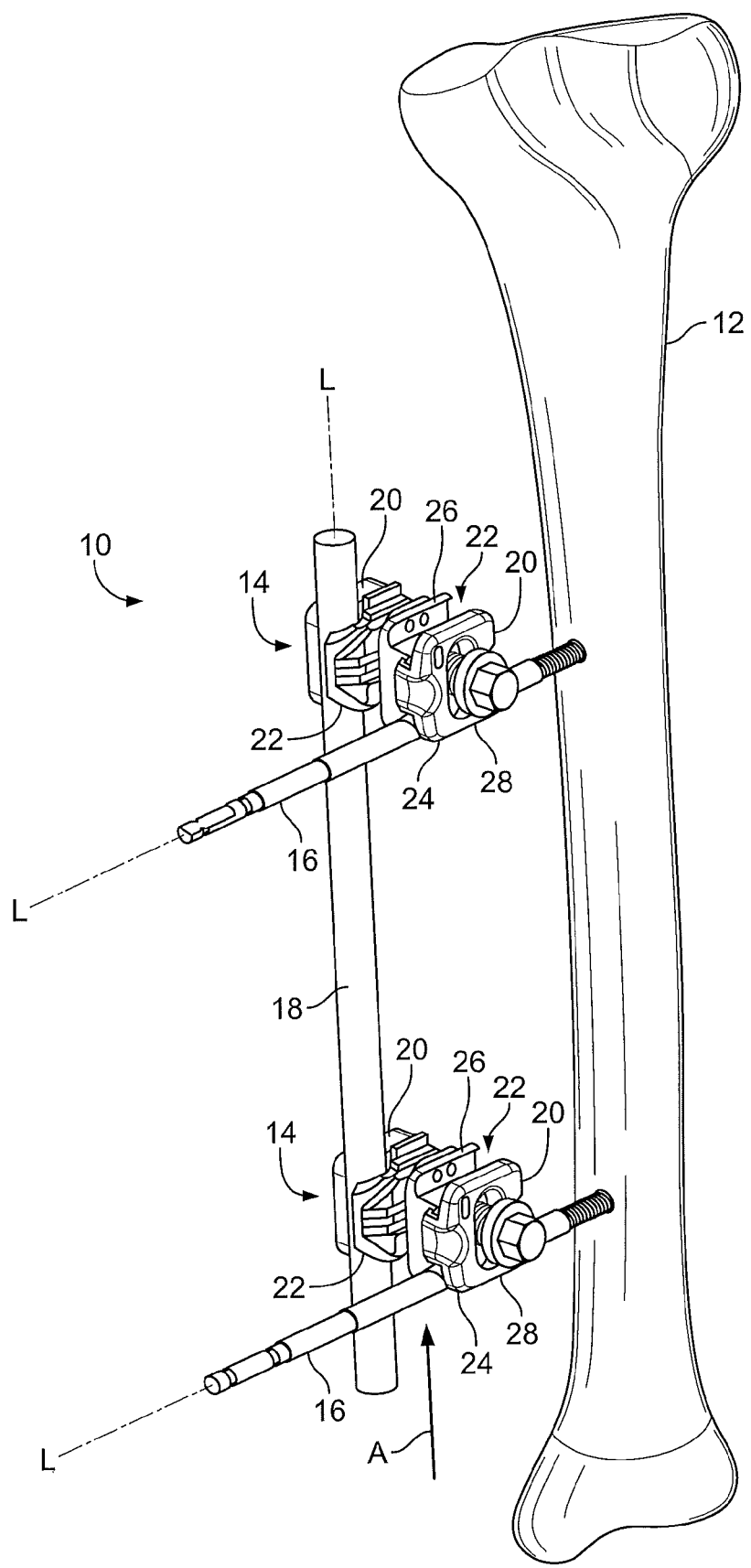
FIG. 1 is a perspective view of an external fixation system.

Referring to FIG. 1, an external fixation system 10 for treating, for example, an injured tibia 12, includes fixation components 14 for connecting a bone pin 16 to a rod 18 of the external fixation system 10. Each fixation component 14 includes two capture members 20. Each capture member 20 defines opposing grooves 22, 24 on opposite lateral sides 26, 28, respectively, of the capture member 20. The groove 24 is sized to capture a first element, for example, a bone pin 16, and the groove 22 is sized to capture a second element having a diameter greater than the diameter of the first element, for example, a rod 18, of the orthopedic fixation system 10 by snapping onto the element from a direction generally perpendicular (see Arrow, A) to a longitudinal axis, L, of the element. The ability of each capture member 20 to receive a bone pin or a rod in opposite grooves provides the external fixation system 10 with versatility when building the frame.

Figure 2:
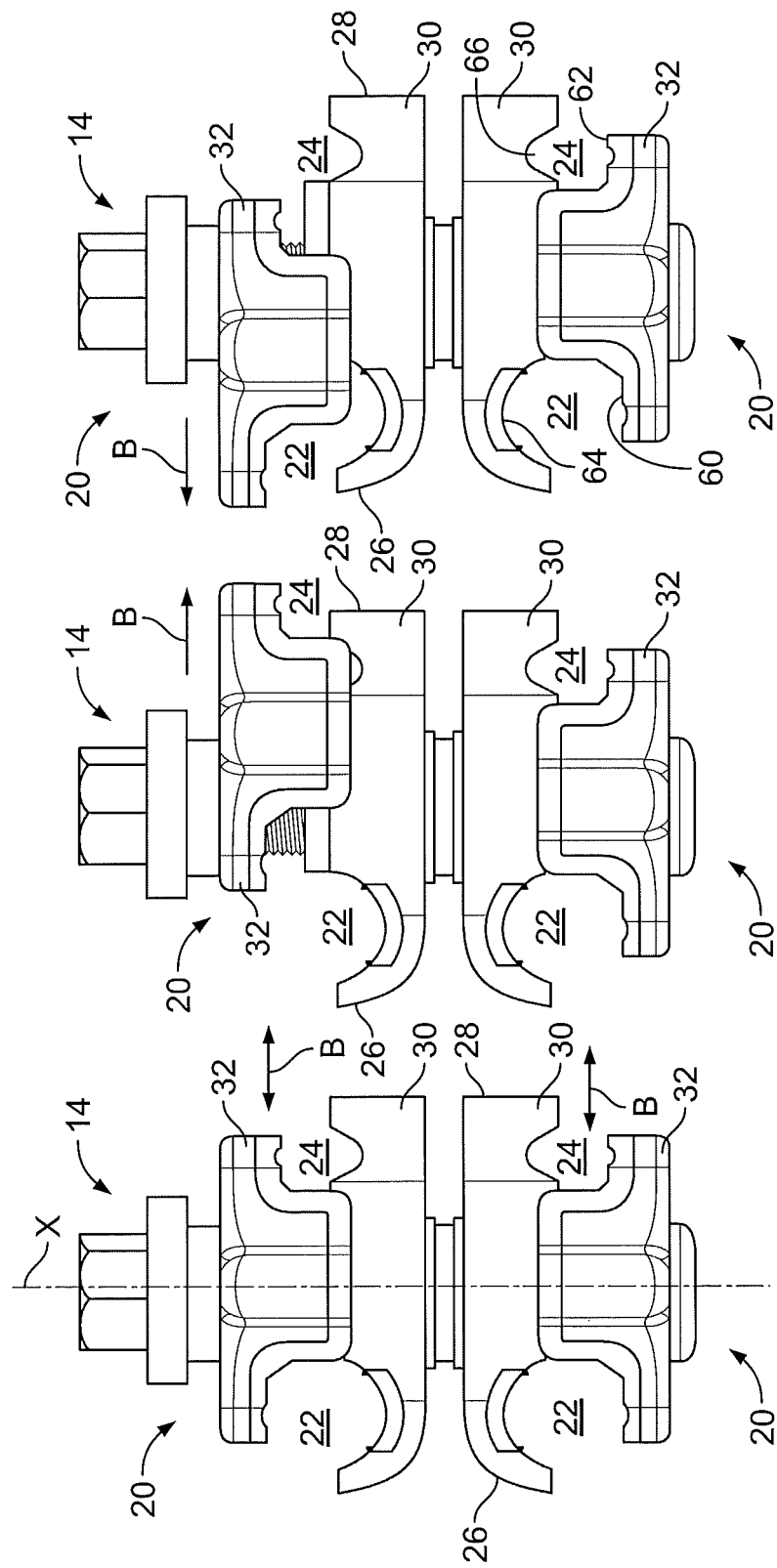
FIGS. 2A-2C are side views of a fixation component of the external fixation system.

Referring also to FIG. 2A, each capture member 20 of the fixation component 14 includes a base 30 and a head 32 coupled to the base 30 to define a component axis, X, that extends through the base 30 and through the head 32. The base 30 and head 32 are coupled for relative lateral translation, arrow, B, between the base 30 and the head 32 in two opposing directions such that a bone pin 16 can be captured by the capture member 20 in the groove 24 (FIG. 2C) or a rod 18 can be captured in the groove 22 (FIG. 2B). The lateral translation in the direction of arrow B is not along the component axis, X, but rather is perpendicular to component axis, X.

FIG. 2B shows the head 32 moved laterally toward side 28 relative to the base 30 along arrow, B, to open the groove 22. In use, this movement is caused by a force exerted on the head 32 by the rod 18. After the rod 18 enters the groove 22, the head 32 is returned to the neutral position of FIG. 2A via a spring force, described below, to close the groove 22 and capture the rod 18.

FIG. 2C shows the head 32 moved laterally toward side 26 relative to the base 30 along arrow, B, to open the groove 24. In use, this movement is caused by a force exerted on the head 32 by the pin 16. After the pin 16 enters the groove 24, the head 32 is returned to the neutral position of FIG. 2A via a spring force to close the groove 24 and capture the pin 16.

Figure 3:
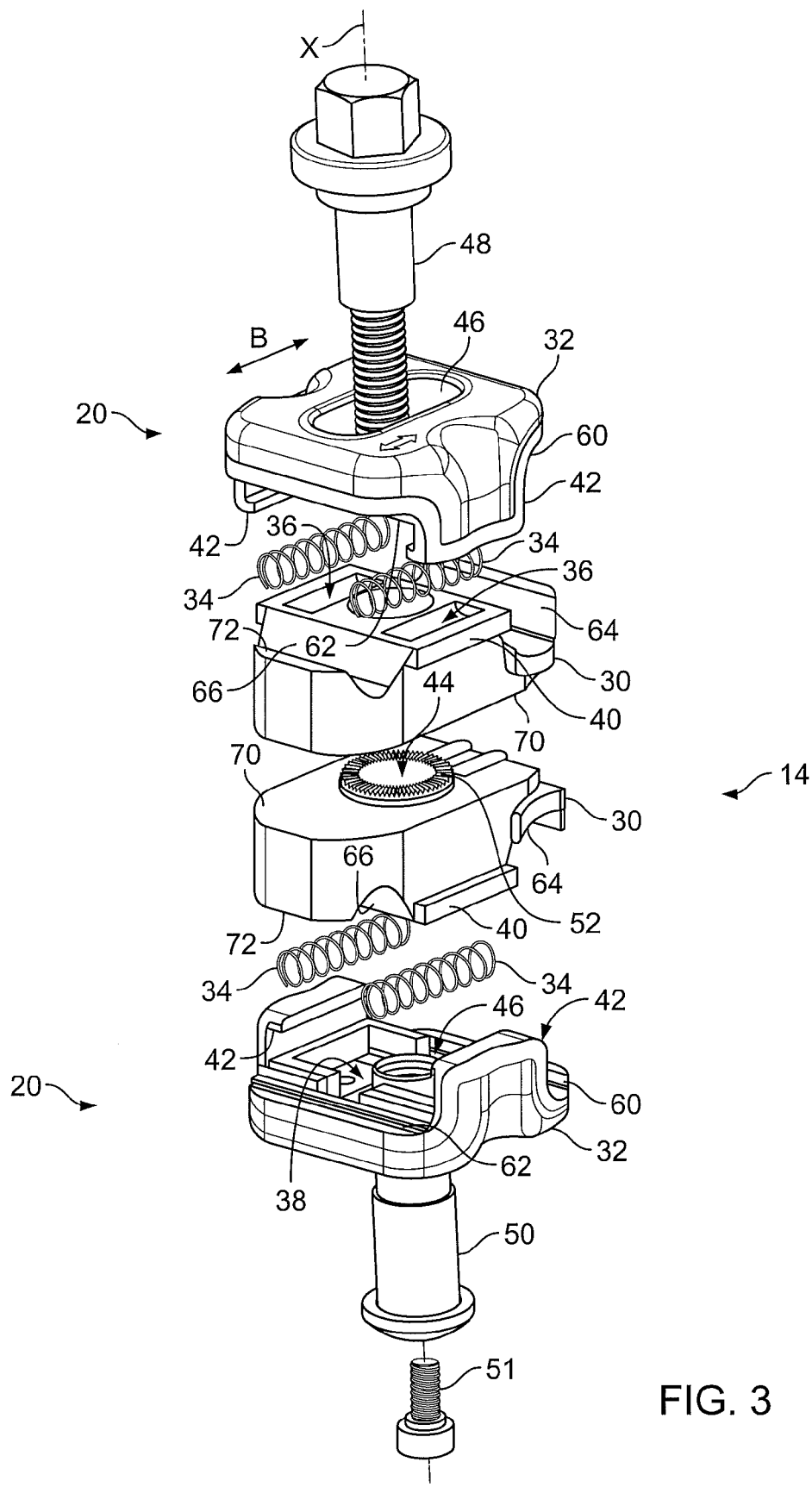
FIG. 3 is an exploded view of the fixation component.

Referring to FIG. 3, the two capture members 20 of the fixation component 14 are coupled together along the component axis, X, by a bolt 48 and an internally threaded receiving shaft 50. Each head 32 has an aperture 46 and each base 30 has an aperture 44 for receiving the bolt 48 and the shaft 50. The aperture 46 is oblong shaped to permit the lateral motion of the head 32, while the aperture 44 is shaped to closely receive the shaft 50 such that lateral motion of the base 30 is limited. Received within the shaft 50 is a screw 51 for securing the fixation component assembly.

The bases 30 have inner sides 70 facing each other and outer sides 72 facing the heads 32. On the inner sides 70 of the bases 30, around the apertures 44, are ridges 52. With the bolt 48 loosened, the two bases can be rotated relative to each other about the component axis, X, to change the relative orientation of the capture members 20. To fix the relative position of the capture members 20 about the component axis, X, the bolt 48 is tightened and the ridges of the two bases 30 engage to lock the capture members in position.

The groove 22 is formed by channels 60 and 64 defined by the head 32 and the base 30, respectively, and the groove 24 is formed by channels 62 and 66 defined by the head 32 and the base 30, respectively. Each capture member 20 includes at least one spring 34, two springs 34 being illustrated, that acts between the base 30 and the head 32. Lateral translation of the head 32 relative to the base 30 in either direction along arrow, B, compresses the spring 34. After the rod or pin is received in the groove, the head 32 is returned to the neutral position due to the force applied to the head 32 as the spring 34 extends. The springs 34 can extend substantially parallel to the direction of relative translation between the head and the base, with the component axis, X, located between the springs 34.

Figure 4:
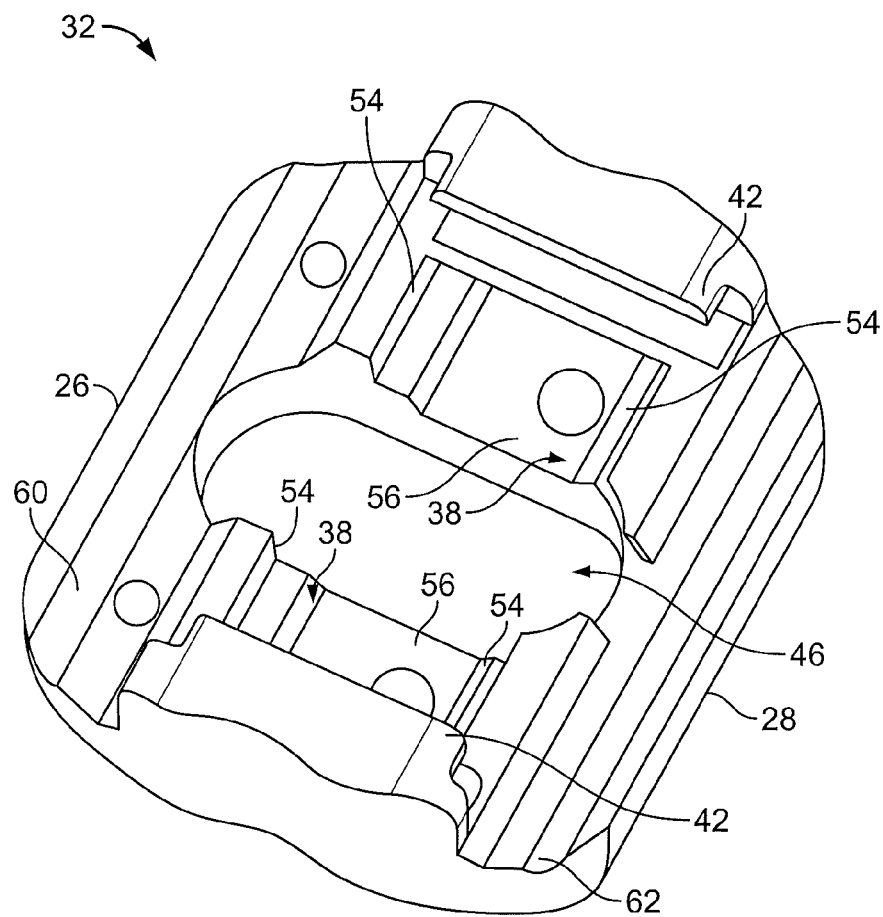
FIG. 4 is a perspective view of a head of a capture member of the fixation component.
Figure 5:
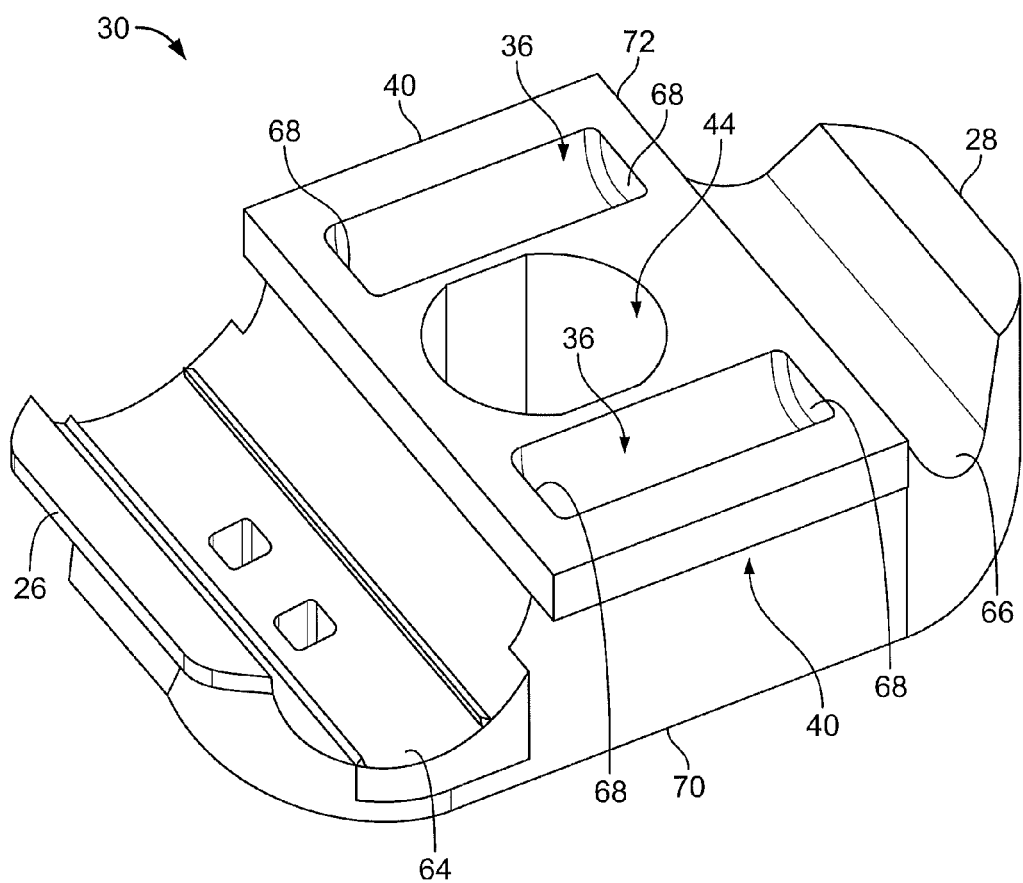
FIG. 5 is a perspective view of a base of the capture member.

Referring to FIGS. 4 and 5, the head 32 includes parallel channels 42 and the base 30 includes parallel rails 40 that are received in the channels 42 to slidably couple the head 32 and the base 30. The engagement between the rails 40 and the channels 42 impedes the head 32 from separating from the base 30 along the component axis, X, and also impedes the head 32 from rotating relative to the base 30. Nevertheless, the channels 42 of the head 32 can slide back and forth along the rails 40 of the base, allowing lateral translation of the head 32 relative to the base 30 along arrow B.

Figure 6:
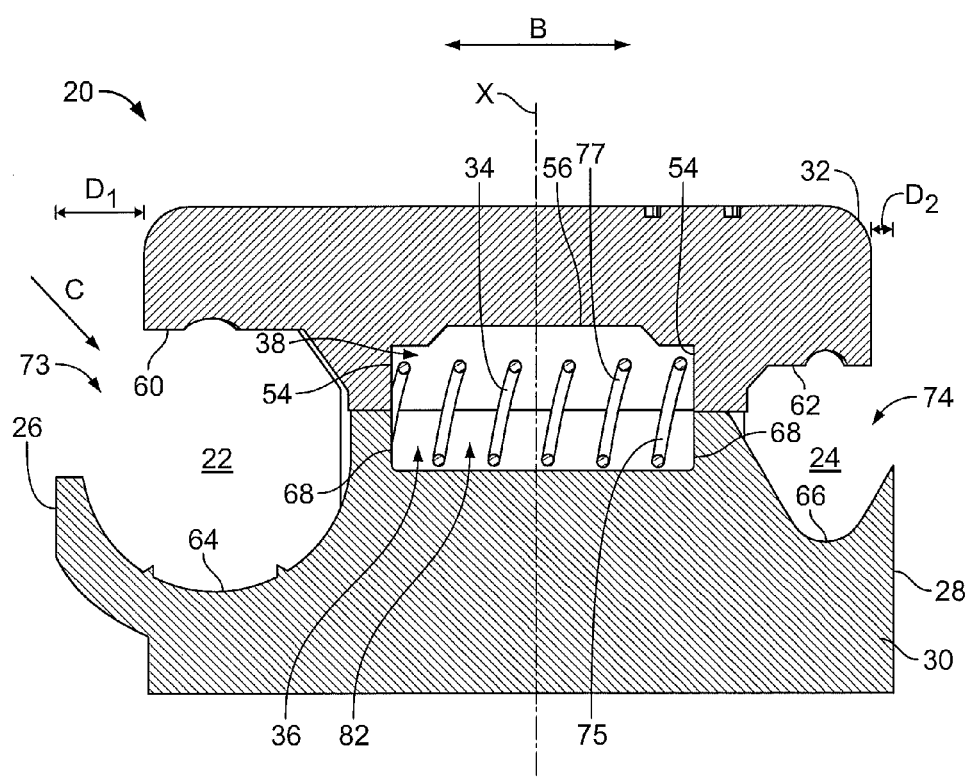
FIG. 6 is a cross-sectional view of the capture member.

The springs 34 are each received within a cavity 82 (FIG. 6) defined by a recess 38 in the head 32 and a recess 36 in the base 30. The head 32 and the base 30 each have two recesses on opposite sides of the apertures 46, 44, such that each capture member 20 defines two cavities 82. The recess 38 is defined between two opposing walls 54, and the recess 36 is defined between two opposing walls 68. The recess 38 may include an optional shelf 56. As shown in FIG. 6, in the neutral position of the capture member 20, the ends of the spring 34 abut the walls 54 of the recess 38 and the walls 68 of the recess 36, with a portion 75 of the spring 34 located in recess 36 and a portion 77 of the spring 34 located in recess 38. When the head 32 is moved laterally along arrow B relative to the base 30, the spring 34 is compressed between one of the walls 54 of the head 32 and an opposite wall 68 of the base 30. In the assembled capture member 20, the springs 34 located between the head 32 and the base 30 couple the head 32 to the base 30 by limiting separation due to relative lateral translation. The optional shelf 56 facilitates assembly of the capture member 20 by providing space for the spring 34 to bend as the head 32 and the base 30 are coupled.

As shown in FIG. 6, the base 30 and the head 32 define an opening 73 at the entrance to the groove 22 and an opening 74 at the entrance to the groove 24. The openings 73, 74 permit a portion of an element to extend into the grooves 22, 24 while the capture member 20 is in the neutral position, stabilizing the element when initially engaged with the capture member 20. When a portion of the element extends through the opening 73, for example, force applied by the element causes the head 32 to laterally translate relative to the base 30 rather than sliding away from the groove 22. The capture member 20 thus guides the element into the groove 22, even when the force applied, for example, in the direction of arrow C, is not precisely directed in a lateral direction.

The base 30 can be sized such that, in the neutral position of the capture member 20, the base 30 extends farther than the head 32 in a lateral direction. One lateral side 26 of the base 30 is longer than the head 32 by a first distance, $D_1$, and the other lateral side 28 of the base 30 longer by a second distance, $D_2$. Because the head 32 is shorter than the base 30, the amount of lateral translation of the head 32 relative to the base 30 needed to open the grooves 22, 24 sufficiently to receive an element is less than the amount that would be required if the head 32 and the base 30 extended an equal distance.

The base 30 and the head 32 can be formed of a metal injection molded component that is partly overmolded with a polymer, for example, a thermoplastic resin or an elastomer. The metal injection molded component provides strength and resistance to creep. The overmolded polymer provides an aesthetic appearance, form control, and reduced cost compared to all-metal construction.

Figure 7B:
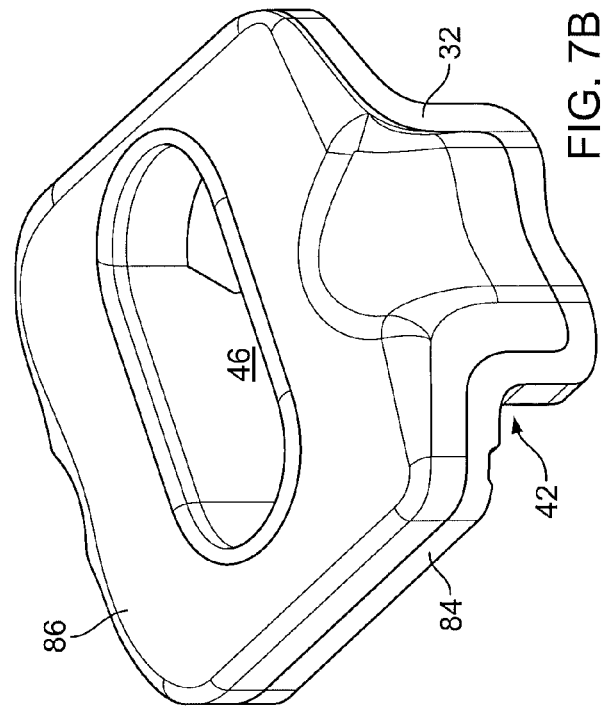
FIGS. 7A-7D are further illustrations of heads of the capture member.
Figure 7A:
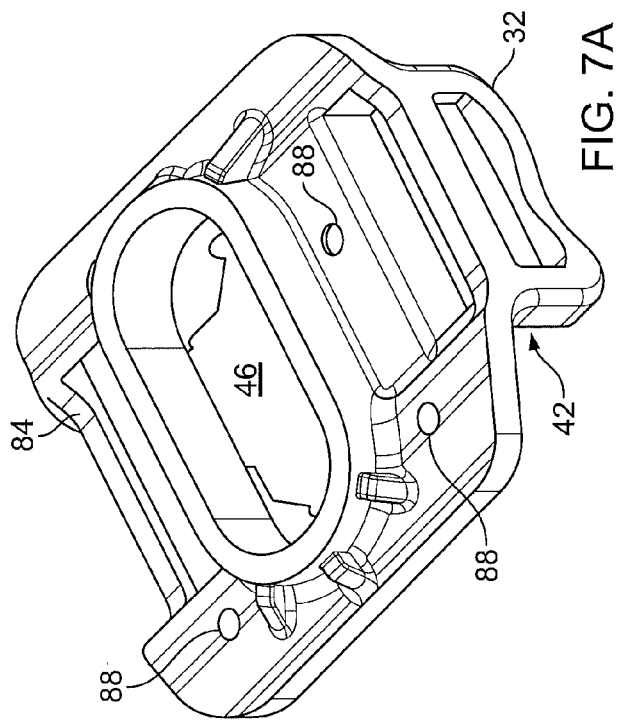
Figure 7D:
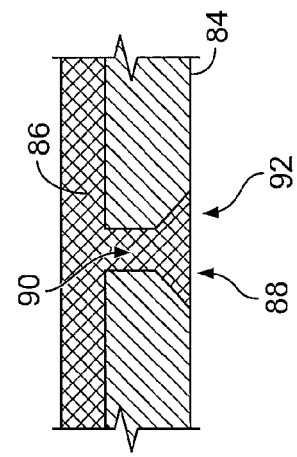
Figure 7C:
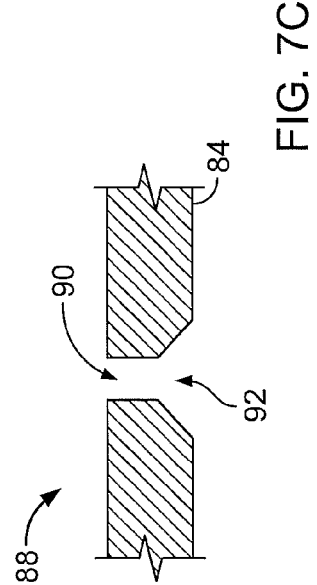

Referring to FIG. 7A, the head 32 is formed by, for example, a metal injection molded stainless steel frame 84. The frame 84 and a polymer coating 86 are illustrated in FIG. 7B. The polymer coating 86 forms part of the exterior surface of the head 32, as discussed below. The frame 84 defines mechanical locks 88 for aiding adhesion of the polymer coating 86 to the frame 84. The mechanical locks 88 are formed, for example, by throughholes 90 having a chamfered end 92 (FIG. 7C). During the overmolding process, the polymer coating enters and fills the throughhole 90 of each mechanical lock 88 to secure the exterior layer 86 to the frame 84 (FIG. 7D).

The base 30 can also be formed from a metal injection molded frame and an overmolded exterior coating as described above for the head 32. Both the head 32 and the base 30 have surfaces of the frame that are not overmolded. For example, the entire surfaces of the head 32 and base 30 that face each other are left uncoated to provide a desired coefficient of friction to hold the rod and pin in the grooves and to permit engagement between the ridges 52 of the base 30 and the head 32.

Other embodiments are within the scope of the following claims. For example, rather than a compression spring, the spring 34 can be a flat spring nested in slots in the base 30. A ball joint can be provided between the two capture members 20 to provide for relative rotation between the capture members 20. Rather than having rails 40, pins can couple the head 32 and the base 30.

Referring again to FIGS. 1 and 2A to 2C, to capture the element 16 using the capture member 20, a user, such as a physician, engages the element 16 with the capture member 20. For example, the element 16 can engage the capture member 20 generally perpendicular to the longitudinal axis, L, of the element 16 at one of the lateral sides 26, 28 of the capture member 20. The user moves the element 16 relative to the capture member 20 while in engagement with the capture member 20 such that the head 32 translates relative to the base 30 in one of the opposing directions. For example, when the element 16 is engaged with the lateral side 28, the head 32 moves in a direction toward the lateral side 26. By causing relative motion of the head 32 and the base 30, the user compresses a spring 14 acting between the head 32 and the base 30.

The user positions the element 16 in one of the grooves 22, 24 of the capture member 20 such that the capture member 20 captures the element 16. For example, the user can position the element 16 in the groove 24 such that the spring 14 moves the head 32 relative to the base 30 to capture the element 16. As the element 16 enters the groove 24, the element 16 disengages from the lateral side 28 of the head 32, permitting the head 32 to translate relative to the base 30 in the other of the opposing directions, toward the lateral side 28. Thus by positioning the element 16 in the groove 24, the user positions the element 16 such that the capture member 20 snaps onto the element 16.

What is claimed is:

1. An external fixation component, comprising:
   a capture member defining opposing grooves on opposite lateral sides of the capture member for capture of an element of an orthopedic fixation system, the capture member comprising:
      a base; and
      a head coupled to the base to define a component axis that extends through the base and through the head,
   wherein, when the capture member is assembled for use, the base and the head are coupled for relative lateral translation in opposing directions toward the opposite lateral sides of the capture member, the base and the head being coupled such that the element can be captured by the capture member in either of the opposing grooves, and
   wherein, when the capture member is assembled for use, the head and the base are coupled such that relative lateral movement of the head and base in either of the opposing directions substantially opens one of the opposing grooves to admit the element.

2. The external fixation component of claim 1, wherein the grooves are each configured to receive one of a bar, a rod, a wire, or a pin.

3. The external fixation component of claim 1, wherein one of the opposing grooves is sized to capture an element having a first diameter, and the opposing groove is sized to capture an element having a diameter greater than the first diameter.

4. The external fixation component of claim 1, wherein the opposing directions are perpendicular to the component axis.

5. The external fixation component of claim 1, further comprising a spring acting between the head and the base.

6. The external fixation component of claim 5, wherein lateral translation of the head relative to the base in each of the opposing directions compresses the spring.

7. The external fixation component of claim 5, wherein the head defines a recess configured to receive a portion of the spring and to permit flexion of the spring within the recess in the direction of relative lateral translation of the base and the head.

8. The external fixation device of claim 5, wherein capture member has a neutral position in which the head and the base are positioned to retain the element in either of the opposing grooves;

wherein the capture member is configured such that relative lateral movement of the head and the base in one of the opposing directions positions the capture member in a first open position in which one of the opposing grooves is opened to permit entry or release of the element; and wherein, in the first open position, the spring biases the head toward the neutral position.

9. The external fixation device of claim 8, wherein the capture member is configured such that relative lateral movement of the head and the base in the other of the opposing directions positions the capture member in a second open position in which the other of the opposing grooves is opened to permit entry or release of the element; and wherein, in the second open position, the spring biases the head toward the neutral position.

10. The external fixation component of claim 1, further comprising:
a second capture member;
a bolt extending along the component axis; and
an internally-threaded receiving shaft extending along the component axis through at least one of the capture members,
wherein the bolt and the receiving shaft couple the capture members along the component axis.

11. The external fixation component of claim 1, wherein the head comprises a metal frame and a portion of the metal frame is overmolded with a polymer coating.

12. The external fixation component of claim 1, wherein the head defines parallel channels and the base includes parallel rails that are received in the channels to slidably couple the head to the base.

13. The external fixation component of claim 12, wherein the engagement between the rails and the channels impedes the head from separating from the base along the component axis and impedes the head from rotating relative to the base.

14. The external fixation component of claim 1, further comprising one or more springs located between the head and the base, wherein the one or more springs are configured to limit separation of the head from the base.

15. The external fixation component of claim 1, wherein the capture member is configured to capture the element by snapping onto the element from a direction generally perpendicular to a longitudinal axis of the element.

16. The external fixation component of claim 1, wherein each groove is defined by channel of the head and a channel of the base.

17. The external fixation component of claim 1, wherein the base and the head are coupled for relative lateral translation in two opposing directions not along the component axis.

18. The external fixation device of claim 1, wherein the capture member has a neutral position in which the capture member is configured to retain the element in either of the opposing grooves; and
wherein, in the neutral position of the capture member, the base extends beyond the head at both of the opposite lateral sides of the capture member.

19. The external fixation device of claim 1, wherein the head defines an oblong aperture to receive a bolt, the oblong aperture including permitting movement of the head with respect to the bolt in the opposing directions while the bolt extends through the oblong aperture in the head.

20. The external fixation device of claim 1, further comprising a spring has a first end, a second end, and extends along a longitudinal axis, wherein the first end of the spring engages a portion of the head and also engages a portion of the base.

21. An external fixation component, comprising:
a capture member defining opposing grooves on opposite lateral sides of the capture member for capture of an element of an orthopedic fixation system, the capture member comprising:
a base; and
a head coupled to the base to define a component axis that extends through the base and through the head,
wherein, when the capture member is assembled for use, the base and the head are coupled for relative lateral translation in opposing directions toward the opposite lateral sides of the capture member, the base and the head being coupled such that the element can be captured by the capture member in either of the opposing grooves;
wherein the capture member has a neutral position in which the capture member is configured to retain the element in either of the opposing grooves; and
wherein, in the neutral position of the capture member, the base extends beyond the head at both of the opposite lateral sides of the capture member.

* * * * *